United States Patent [19]

Liboff et al.

[11] Patent Number: 5,458,558
[45] Date of Patent: * Oct. 17, 1995

[54] METHOD FOR CONTROLLING TISSUE GROWTH WITN AN APPLIED FLUCTUATING MAGNETIC FIELD

[75] Inventors: Abraham R. Liboff, Birmingham, Mich.; Bruce R. McLeod; Stephen D. Smith, both of Bozeman, Mont.

[73] Assignee: Life Resonances, Inc., Bozeman, Mont.

[ * ] Notice: The portion of the term of this patent subsequent to Jun. 12, 2007 has been disclaimed.

[21] Appl. No.: 136,464

[22] Filed: Oct. 13, 1993

Related U.S. Application Data

[63] Continuation of Ser. No. 861,673, Apr. 1, 1992, Pat. No. 5,269,745, which is a continuation of Ser. No. 496,415, Mar. 20, 1990, Pat. No. 5,123,898, which is a continuation of Ser. No. 172,268, Mar. 23, 1988, Pat. No. 4,932,951.

[51] Int. Cl.⁶ ........................................ A61N 1/00
[52] U.S. Cl. ................................... 600/13; 607/51
[58] Field of Search ....................... 600/9–15; 607/50–52

[56] References Cited

U.S. PATENT DOCUMENTS 4,266,532   5/1981   Ryaby et al. ............................. 600/14
4,548,208  10/1985   Niemi ..................................... 600/14

Primary Examiner—Lee S. Cohen
Assistant Examiner—John P. Lacyk
Attorney, Agent, or Firm—Dykema Gossett

[57] ABSTRACT

An apparatus and method for regulating tissue growth in vivo are provided. The apparatus includes a magnetic field generator and a magnetic field detector for producing a controlled, fluctuating, directionally oriented magnetic field parallel to a predetermined axis projecting through the target tissue. The field detector samples the magnetic flux density along the predetermined access and provides a signal to a microprocessor which determines the average value of the flux density. The applied magnetic field is oscillated at predetermined frequencies to maintain a preselected ratio of frequency to average flux density. This ratio is maintained by adjusting the frequency of the fluctuating magnetic field and/or by adjusting the intensity of the applied magnetic field as the composite magnetic flux density changes in response to changes in the local magnetic field to which the target tissue is subjected. By maintaining these precise predetermined ratios of frequency to average magnetic flux density, growth characteristics of the target tissue are controlled.

1 Claim, 3 Drawing Sheets

METHOD FOR CONTROLLING TISSUE GROWTH WITN AN APPLIED FLUCTUATING MAGNETIC FIELD

This is a continuation of application Ser. No. 07/861,673 filed on Apr. 1, 1992, now U.S. Pat. No. 5,269,745, which is a continuation application of U.S. Ser. No. 07/496,415 filed Mar. 20, 1990, now U.S. Pat. No. 5,123,898 which is a continuation application of U.S. Ser. No. 07/172,268 filed Mar. 23, 1988, now U.S. Pat. No. 4,932,951.

FIELD OF THE INVENTION

The present invention relates generally to methods and apparatus for controlling growth characteristics of living tissue. More specifically, the present invention relates to non-invasive techniques for mediating tissue growth, maintenance and repair.

BACKGROUND OF THE INVENTION

Tissue and cell development have been studied extensively to determine the mechanisms by which maturation, maintenance, and repair occur in living organisms. Generally, development of a cell or tissue can be considered as a transformation from one state or stage to another relatively permanent state or condition. Development encompasses a wide variety of developmental patterns, all of which are characterized by progressive and systematic transformation of the cells or tissue.

In many instances it is desirable to control or alter the development of cells and tissue in vivo to enhance the quality of life for higher organisms such as man. To this end, science has struggled to provide means by which the natural order of an organism can be maintained or restored in defiance of a debilitating injury, disease or other abnormality. While some prior art therapies have been successful, others have failed to reach their full potential due to unwanted side effects, inferior results, or difficult implementation.

As will be appreciated by those skilled in the art, tissue and organ development involve complex processes of cellular growth, differentiation and Interaction mediated by complex biochemical reactions. At the genetic level, development is regulated by genomic expression; at the cellular level, the role of membrane interaction with the complex biochemical milieu of higher organisms is instrumental in developmental processes. Moreover, "remodeling" of tissues or organs is often an essential step in the natural development of higher organisms.

In recent years, multidisciplinary investigations of developmental processes have provided evidence suggesting that electric and magnetic fields play an important role in cell and tissue behavior. In U.S. patent application Ser. No. 923,760, entitled, "Techniques for Enhancing the Permeability of Ions," which has been assigned to the assignee of the present invention and the disclosure of which is incorporated herein by reference, a method and apparatus are disclosed by which transmembrane movement of a preselected ion is magnetically regulated using a time-varying magnetic field. The fluctuating magnetic field is tuned to the cyclotron resonance energy absorption frequency of the preselected ion. This important discovery brought to light the interplay of local geomagnetic fields and frequency dependence in ion transport mechanisms. It has now been discovered that by utilizing and extending the principles of cyclotron resonance tuning, an unexpected and remarkable advance in the control and modification of developmental processes in living tissue can be achieved.

Currently, research efforts in the area of electronic medical devices which affect growth mechanisms in living systems have focused on strain-related bioelectrical phenomena that have been observed i-n tissue such as bone, tendon and cartilage. During the last few decades, others have noted that electrical potentials are produced in bone in response to mechanical stress. It has been postulated that these electrical potentials mediate the stress-induced structural changes in bone architecture which were observed almost a century ago by J. Wolfe. Hence, although bioelectrical potentials are not well understood, numerous attempts have been made to induce tissue growth with electrical potentials and currents. Much of this work has dealt with the repair of bone non-unions, i.e. bone fractures which have not responded to traditional therapies.

Bone formation, as will be known by those skilled in the art, is a complex biological process. It involves the interaction of several characteristic cell types, including monocytes, osteoblasts, osteoclasts, osteocytes, chondrocytes, fibroblasts and undifferentiated bone mesenchymal cells which form a hard intercellular matrix of collagen and mineral crystals in which bone cells are embedded. The matrix is synthesized by osteoblasts which extrude collagen and mucopolysaccharide. By a process which is not fully understood, crystal nuclei form in the matrix to promote rapid mineralization by inorganic salts. Bone formation proceeds outward from ossification sites defined by clusters of osteoblasts. Osteoclasts then resorb bone during remodeling, whereby the bone architecture is restructured to provide maximum strength.

A number of bone disorders are known in which the integrity of the bone structure is compromised. Bone fractures produced by accidental trauma are quite common. The treatment of bone fractures may be complicated by delayed union of the Fractured ends, by bone non-union, or by abnormal unions such as pseudarthroses. Moreover, in certain bone diseases, excess bone tissue is formed (osteophytes; osteosclerosis) which interferes with normal function. Alternatively, a shortage of bone tissue (osteopenia) may occur which decreases the fracture resistance of bone. A widespread, generalized form of osteopenia known as osteoporosis is characterized by a reduction in bone density accompanied by increased porosity and brittleness. Osteoporosis is associated with a loss of calcium from bone and is a major concern of the elderly, a group in which the disease is most prevalent. Osteoporosis significantly increases susceptibility to bone fractures and is generally considered to be the most common bone disease in humans. Other maladies such as osteomalacia, Paget's disease, osteomyelitis and osteoarthritis are also well documented in medical literature.

A number of devices and techniques have been used by others with varying degrees of success to treat bone disorders. These include traction, splints, casts and internal fixation by pins and plates to repair bone fractures. Abnormal bone growth has been successfully interrupted by the fusion of epiphysis to the bone shaft in a process referred to as "epiphysiodesis." Bone grafts have also been attempted with limited success. In some instances, where other treatment modalities fail, amputation the affected limb is performed as a last resort.

More recently, methods have been explored by others for altering the electrical environment of bone tissue in an attempt to stimulate bone growth in fracture repair. These efforts originally concentrated on the use of electrode implants by which direct current was flowed across or into a bone non-union or abnormal union to stimulate repair. Due to numerous drawbacks, including the associated risks of surgery required to implant the electrodes, alternate, non-invasive techniques were pursued. While capacitively-generated electrostatic fields provided some beneficial results, the relatively large fields necessary were generally prohibitive. Finally, alternating, high-intensity electromagnetic fields were utilized to induce a voltage in bone. It was believed that by using the affected bone as a conductor, current flow through the bone could be induced which would produce therapeutic benefits.

These prior art inductive devices are typified by the apparatus disclosed in U.S. Pat. No. 3,893,462 to Manning entitled, "Bioelectrochemical Regenerator and Stimulator Devices and Methods for Applying Electrical Energy to Cells and/or Tissue in a Living Body" and the devices set forth in U.S. Pat. No. 4,105,017 to Ryaby et al. entitled, "Modification of the Growth Repair and Maintenance Behavior of Living Tissue and Cells by a Specific and Selective Change in Electrical Environment." These investigators have focused on the use of large fields to produce high induced currents in living tissue with well-defined "therapeutic" waveforms. The inventors of the present invention have approached the problem of regulating tissue growth from a different perspective. In its preferred embodiment, the present invention utilizes the interaction of fluctuating magnetic fields and preselected ions present in biological fluids to influence developmental processes. Although a possible role of magnetic fields beyond the galvanic action of induced currents is briefly mentioned in U.S. Pat. No. 3,890,953 to Kraus et al., to Applicants' knowledge no investigator has previously controlled bone growth in the manner set forth in the present invention.

SUMMARY OF THE INVENTION

In one aspect, the present invention provides an apparatus for controlling the growth of living tissue. The novel apparatus includes magnetic field generating means such as a field coil for generating a controlled, fluctuating magnetic field which penetrates a tissue in vivo, and an associated magnetic field sensing device for measuring the intensity of the magnetic field present in the tissue. In one embodiment, the magnetic field generating means and magnetic field sensor are enclosed within a housing along with a power source such as a battery or the like. In operation, the magnetic field generating means is positioned adjacent to a region of living tissue in a subject, the growth characteristics of which are to be controlled. A fluctuating, directional magnetic field is then generated by the magnetic field generating means. The applied magnetic flux density is directed along a predetermined axis which passes through the tissue to be affected. In one embodiment, the applied magnetic flux density along the axis is superimposed on that component of the local or ambient magnetic field which is parallel to the predetermined axis to create a fluctuating composite field. The resultant combined magnetic flux density which is parallel to the predetermined axis and which passes through the tissue to be affected is measured by the magnetic field sensor. The magnetic field sensor determines the net average value of the magnetic flux density which passes through the targeted tissue along the predetermined axis. In one embodiment, the frequency of the fluctuating magnetic field is set at a predetermined value and the net average value of the magnetic flux density is then regulated by adjusting the magnitude of the applied magnetic field to produce a combined magnetic field having a preselected ratio of frequency-to-field magnitude which affects the growth characteristics of the target tissue. In a preferred embodiment, changes in the magnitude of the local magnetic field along the predetermined axis which would otherwise alter the magnetic flux density of the combined magnetic field parallel to the predetermined axis and which would thus produce a deviation from the desired ratio are counterbalanced by adjustment of the magnitude of the applied, fluctuating magnetic field. This adjustment is preferably made by microprocessing means in association with both the magnetic field generating means and the magnetic field sensor. Preferred ratios of frequency-to-field magnitude are determined with reference to the equation:

$$f_c/B = q/(2\pi m)$$

where $f_c$ is the frequency of the combined magnetic field in Hertz, B is the non-zero average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla. In one embodiment, the values of q and m are selected with reference to the charge and mass of a preselected ion.

In another embodiment, changes in the ambient magnetic field which would otherwise alter the ratio or frequency-to-magnetic field are counterbalanced by adjusting the frequency of the applied magnetic field to maintain the preferred ratio. The present invention also contemplates the adjustment of both frequency and field magnitude to maintain the predetermined preferred ratio. Preferably, the peak-to-peak amplitude of the AC component is in the range of about $2.0 \times 10^{-5}$ to about $6.0 \times 10^{-5}$ Tesla. The waveform is preferably substantially sinusoidal, but other waveforms are suitable.

The present invention also provides a method of controlling the growth characteristics of living tissue which includes in one aspect the steps of generating a fluctuating, directionally-oriented magnetic field; positioning a region of living tissue of subject, within the fluctuating, magnetic field so that the field passes through the target tissue parallel to a predetermined axis that extends through the tissue; measuring the net average value of the combined magnetic flux density parallel to the predetermined axis through the tissue, where the combined magnetic field is the sum of the local magnetic field along the predetermined axis and the applied magnetic field; adjusting the frequency and/or magnitude of the applied magnetic field to produce a combined magnetic field along the axis having a predetermined ratio of frequency-to-magnitude, where the predetermined ratio influences the growth characteristics of the target tissue; maintaining the predetermined ratio of frequency to magnitude of the combined field; and exposing the target tissue to the combined magnetic field for a period of time sufficient to affect the growth characteristics of the tissue. Other relationships between frequency and magnitude may be useful or even desirable in a particular application.

The present invention is particularly suitable for enhancing the growth of bone and cartilage to repair recalcitrant fractures and damaged cartilage surfaces. These and other advantages of the present invention will become more apparent from the following description of preferred embodiments and with reference to the drawings in which:

DETAILED DESCRIPTION OF THE PREFERRED EMBODIMENTS

Figure 1:
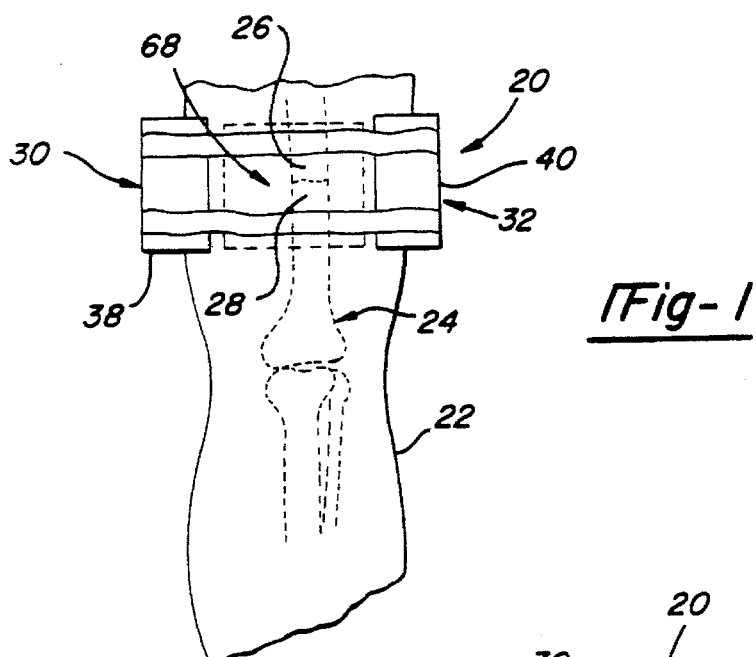
FIG. 1 is a front elevational view of the present invention as applied to the treatment of a fractured femur.

Referring now to FIG. 1 of the drawings, tissue growth regulator 20 is shown in position on leg 22 of a subject. It is to be understood that both the apparatus and the method of the present invention are suitable for use in controlling tissue growth in an animal subject or a human subject. Thus, the target tissue which is to be controlled, is a region of living tissue in a subject, in other words, an "in vivo" target tissue. As used herein, the term "living tissue" shall be defined, without limiting its customary meaning, as tissue which is capable of conducting metabolic functions such as cellular respiration and which possesses viable growth characteristics. "Growth characteristics" shall be defined, without limiting its customary meaning, as those attributes of living tissue which serve to mediate replication, growth, maintenance and repair. Although the stimulation of tissue growth will be emphasized in this description of preferred embodiments of the present invention, it is to be understood that the present invention can also be used to retard or impede the development of living tissue and may be suitable for other applications, including the prevention of abnormal tissue development.

Fractured femur 24 is shown having fracture surfaces or ends 26 and 28 which are to be stimulated by the present invention to enhance the rate at which the bone fracture heals. As previously mentioned, the natural developmental processes by which ends 26 and 28 reunite may be interrupted by a factor of known or unknown etiology resulting in a delayed union, abnormal union, or bone non-union. The present invention is particularly suitable for use in the treatment of bone non-unions. In this embodiment, tissue growth stimulator 20 includes two treatment heads 30 and 32 which are positioned on leg 22 in the region of ends 26 and 28 in the opposed fashion illustrated in FIG. 1. As will be explained more fully, it is important that treatment heads 30 and 32 be placed adjacent the target tissue such that the tissue is within the range of the magnetic flux generated by the treatment heads. Also, although it is preferred that two treatment heads be employed in an opposed fashion as illustrated in FIG. 1, a single treatment head or a plurality of treatment heads greater than two may be suitable in some applications.

Figure 2:
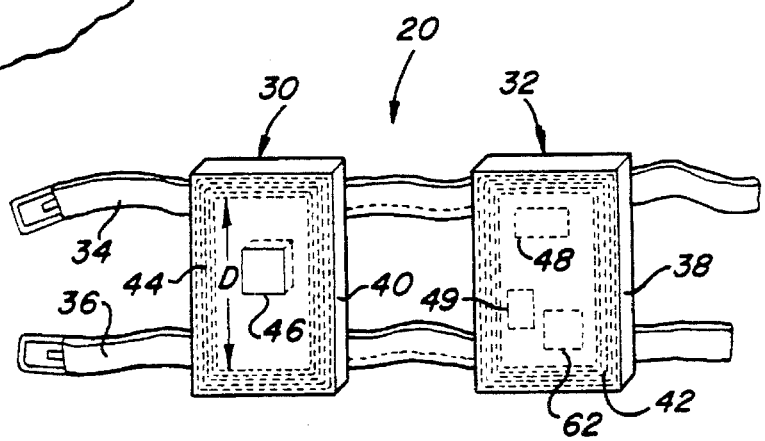
FIG. 2 is a front elevational view of the present invention with two treatment heads having field coils and magnetic field sensing means shown in phantom.

Referring now to FIG. 2 of the drawings, retaining straps 34 and 36 are seen by which tissue growth regulator 20 is preferably secured into position on leg 22. Other securing means may be suitable or desirable in a particular application. It may also be desirable to provide tissue growth regulator 20 as a stationary unit or the like as an alternative to the mobile unit depicted in FIGS. 1–3. Straps or belts 34 and 36 are attached to treatment heads 30, 32 by any convenient means, preferably in a manner which allows the distance between treatment heads 30, 32 to be adjusted to be obtain the substantially opposed orientation shown in FIG. 1. Hence, it is preferred that straps 30, 32 permit adjustment sufficient for tissue growth regulator 20 to be used on limbs of various sizes. Treatment heads 30 and 32 should be snugly but comfortably in position to prevent substantial movement relative to the target tissue, illustrated here as fracture ends 26 and 28. It is anticipated that the present invention will be useful in conjunction with conventional plaster or plastic casts wherein tissue growth regulator 20 may be integrated directly into the cast architecture or may be mounted on the extension of the cast.

Figure 3:
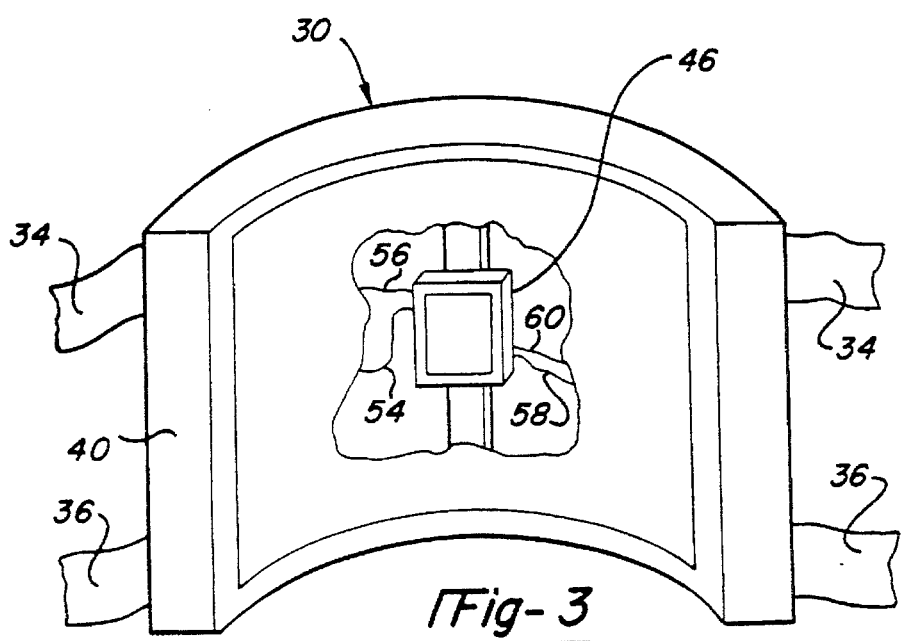
FIG. 3 is a front elevational view of one treatment head of the present invention with the housing broken away to illustrate the magnetic field sensing means.

Referring now to FIGS. 2 and 3, each treatment head 30, 32 includes a housing 38, 40 of a non-magnetic material such as plastic which encloses a field coil 42, 44. In addition, it is preferred that at least one treatment head enclose a magnetic field sensing device 46, such as a Hall-effect device, shown enclosed within housing 40 of treatment head 30. Power source 48 is provided, preferably enclosed within one of the treatment heads. Power source 48 may comprise a dry cell battery or the like. It is preferred that two or more separate power sources be provided to minimize the number of circuit elements required. Housing 38 is also preferably provided with means by which battery 48 can be accessed such as a sliding panel or the like (not shown) to facilitate installation. It may also be suitable to mount battery 48 on the outside of housing 38 or to provide some other external arrangement. While it is a significant feature and advantage of the present invention to provide a tissue growth regulator which includes a self-contained power source, and thus which is both lightweight and mobile, other power sources such as an ac line source may be used in connection with an ac/dc converter where mobility is not required.

Field coils 44 and 42 are the preferred means by which an applied magnetic field is generated in the present invention. The radius of each field coil 44 and 42, as well as the turns of winding, may vary in accordance with the principles of the present invention. Those skilled in the art will appreciate that other electromagnets or possibly permanent magnets may be adapted for use in the present invention and any such use is intended to come within the scope of the present invention. Field coils 44 and 42 are most preferred since they provide a simple means for concentrating magnetic lines of force. Also, the present invention includes several components within a single housing, and therefore shielding may be employed to prevent undesired interactions between components.

Figure 4:
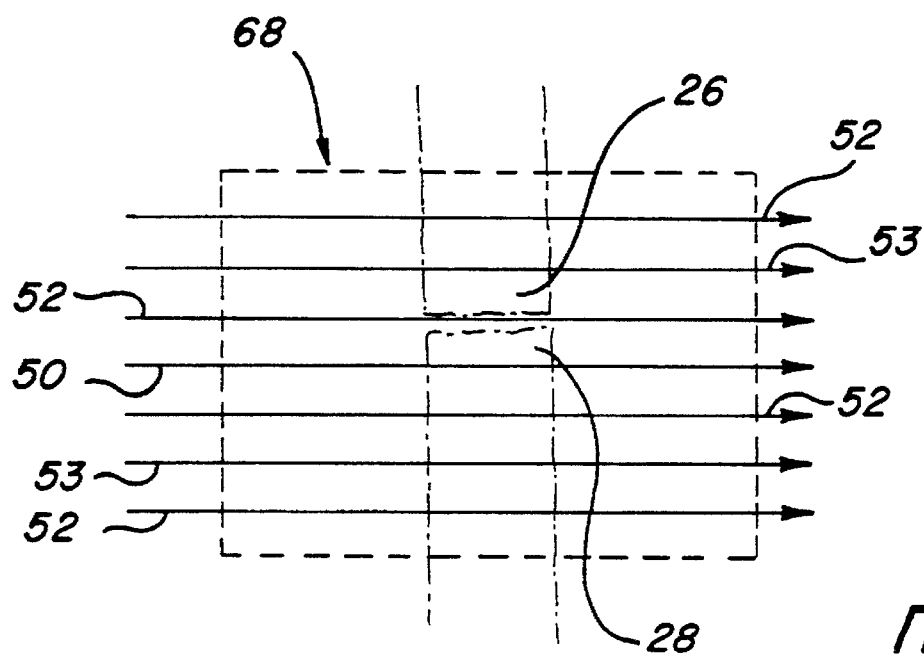
FIG. 4 illustrates the combined magnetic flux of the present invention with changes in intensity over time.

In the most preferred arrangement, the geometry and relative position of field coils 44, 42 during treatment are such that field coils 44, 42 operate as Helmholtz coils. Those skilled in the art will thus appreciate that in the most preferred arrangement, field coils 44, 42 are substantially identical, field-aiding, parallel coaxial coils separated by a distance equal to the radius of each coil. In this most preferred embodiment, the Helmholtz configuration produces an applied magnetic field in a predetermined space between the coils. Referring to FIG. 4, this predetermined space 68 is occupied by the target tissue, the growth characteristics of which are regulated by the present invention. This concept will be more fully explained herein. Hence, predetermined space 68 is shown through which magnetic field lines 52 extend parallel to predetermined axis 50.

Hence, magnetic field lines 52 pass through the target tissue, which is illustrated here as fracture ends 26, 28.

It will be appreciated that the target tissue will be subject to local magnetic influences. As used herein, "local magnetic field" shall be defined as the magnetic influences, including the earth's magnetic field or geomagnetic field, which create a local magnetic flux that flows through the target tissue. "Magnetic flux density" shall be defined in the customary manner as the number of magnetic field lines per unit area of a section perpendicular to the direction of flux. Factors contributing to the local magnetic field in addition to the geomagnetic field may include localized regions of ferromagnetic materials or the like. In one embodiment of the present invention, field coils 42 and 44 are used to create an applied, fluctuating magnetic field which when combined with the local magnetic field parallel to predetermined axis 50 produces a resultant or combined magnetic field having a precisely controlled, predetermined ratio of magnetic flux density to frequency.

Referring now to FIG. 3 of the drawings, magnetic field sensing device or magnetometer 46 is shown in housing 40 with the appropriate leads 54, 56, 58 and 60, by which the field-sensing device is electrically connected to power source 48 and in one embodiment to microprocessing means 62. As will be appreciated by those skilled in the art, the Helmholtz configuration of field coils 42, 44 provides a substantially uniform or equal applied magnetic field in active volume or predetermined space 68 between the coils. Hence, tissue growth regulator 20 allows a substantially uniform applied magnetic field to be applied to the target tissue in predetermined space 68. The direction of the applied magnetic flux defines the direction of predetermined axis 50. That is, the flux of the applied magnetic field is always in the same direction as predetermined axis 50. In the preferred embodiment of the invention, this applied magnetic flux is superimposed on the local magnetic flux in predetermined space 68. The field lines of this local flux component are shown by reference numeral 53.

Magnetometer 46 is positioned in growth regulator 20 to measure the total or composite magnetic flux which passes through predetermined space 68 parallel to predetermined axis 50. It will be understood, then, that magnetometer 46 is provided to measure the composite magnetic field along axis 50. The local field component either augments or decreases the applied magnetic flux unless the local field component is zero. This is an important feature of the present invention. The relatively low applied flux densities and precise predetermined relationships of combined flux density and frequency provided by the present invention must be maintained during treatment, notwithstanding the influence of the local magnetic field. This is achieved in essentially two preferred manners which will be explained more fully herein. Thus, magnetometer 46 is provided to determine the magnitude of the magnetic flux density of the local magnetic field. Hence, in one embodiment of the invention, predetermined space 68 is occupied by a region of living tissue of a human or animal subject. Predetermined axis 50 which projects through predetermined space 68 and thus through the target tissue is defined by the relative position of tissue growth regulator 20 with respect to the target tissue. Predetermined axis 50 is in the same direction as the applied magnetic flux generated by field coils 42, 44 through predetermined space 68. During this procedure, magnetometer 46 measures the total magnetic flux density parallel to predetermined axis 50 which passes through the target tissue. This total or composite magnetic flux density is the sum of the applied component and the local component. The local component may at times be in the same direction as the applied flux and at other times be in directions other than the applied flux. At times the local component may also be zero. These changes in the local component along the axis are produced by changes in the direction of predetermined axis 50 as tissue growth regulator 20 is repositioned such as when an ambulatory patient receiving treatment moves leg 22. Thus at $T_1$ the applied flux generated by field coils 42, 44 may be parallel to a north-south axis, perhaps when the patient faces west. Since the direction of predetermined axis 50 is defined by the direction of the applied flux, in this position, predetermined axis 50 is therefore also in the north-south direction. At $T_2$, the patient may turn to the north causing a 90 degree rotation of field coils 42, 44 such that the applied magnetic flux is now parallel to an east-west axis. Accordingly, predetermined axis 50 is then also in the east-west direction. In most cases, the local component will be different in different directions; hence the composite flux measured by magnetometer 46 along predetermined axis 50 will change in response to changes in the position of tissue growth regulator 20 with respect to the local magnetic field. The net average value of magnetic flux density is accordingly regulated to adjust to the change in composite flux. Therefore, growth regulator 20 is preferably a mobile unit which is a significant advantage.

Figure 5:
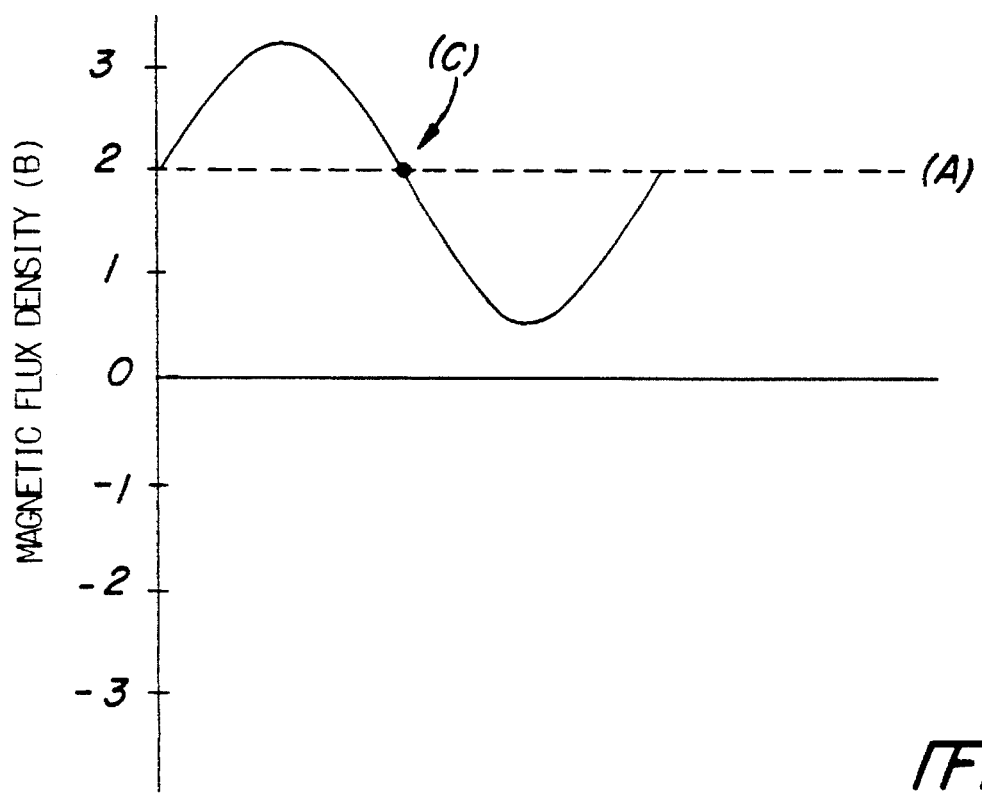
FIG. 5 illustrates the fluctuating, non-zero average value of the combined magnetic flux density.

The unexpected and superior results of the present invention are achieved by creating a fluctuating combined or composite magnetic field having a magnetic flux density parallel to predetermined axis 50, where the combined magnetic flux density along axis 50 is maintained at a predetermined relationship to the frequency of the fluctuations. In this embodiment, the combined magnetic flux density parallel to predetermined axis 50 has a non-zero net average value. As illustrated in FIG. 5 of the drawings, the therapeutic magnetic field of the present invention can be thought of as a static field having reference level A on which a fluctuating magnetic field is superimposed. It comprises an ac component which varies in amplitude but not direction and a dc reference around which the ac component varies. Reference level A is the non-zero average value of the flux density (B). Therefore, it will be understood that the non-zero average or net average value of the composite magnetic flux density along predetermined axis 50 is utilized since the magnitude B of the composite flux density changes at a predetermined rate due to oscillation or fluctuation of the applied magnetic flux. Thus, an average value is utilized which is a non-zero average value illustrated at point (c). This reflects that although the composite magnetic flux density along the axis is oscillating at a controlled rate, the composite field is regulated by the intensity of the applied field to ensure that the composite field is always unipolar; that is, the composite field is always in the same direction along predetermined axis 50.

As stated, it has been found that rather precise relationships of the flux density of the combined magnetic field to the frequency of the fluctuations are used in the present invention to provide therapeutic results. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the combined magnetic field parallel to predetermined axis 50 in Tesla, q/m has a value of from about $5 \times 10^5$ to about $100 \times 10^6$ Coulombs per kilogram. B preferably has a value not in excess of about 5×10$^{-4}$ Tesla. To stimulate bone growth, as an example, the following frequency and associated combined magnetic flux density (B) is preferred:

| fc (Hertz) | B (Tesla) |
|---|---|
| 16.0 | 2.09 × 10$^{-5}$ |

To retard bone growth, the following frequency and associated combined magnetic flux density (B) is preferred:

| fc (Hertz) | B (Tesla) |
|---|---|
| 16.0 | 4.09 × 10$^{-5}$ |

While the exact mechanism by which growth characteristics of the target tissue are affected by the present invention is not fully understood, as will be explained more fully in connection with the method of the present invention, remarkable results are achieved by tuning the combined field to resonant absorption frequencies of preselected ions.

Therefore, it will be readily understood by those skilled in the art that tissue growth regulator 20 includes in one aspect a magnetic field generating means for providing an oscillating magnetic field parallel to a predetermined axis. Magnetic growth regulator 20 also preferably includes magnetic field sensing means by which the magnetic flux density parallel to the predetermined axis is measured. A microcontrolling means is also preferably provided in tissue growth regulator 20 by which a predetermined relationship between the magnetic flux density parallel to the predetermined axis and the frequency of the magnetic field oscillation is created and maintained as tissue growth regulator 20 changes orientation with respect to the local magnetic field. Tissue growth regulator 20 is thus used to create, monitor and adjust a magnetic field of predetermined parameters in predetermined volume 68. While this predetermined relationship is preferably maintained by adjusting the applied flux to compensate for changes in the local field component, alternatively the frequency can be adjusted to preserve the desired ratio.

In use, living tissue is placed within predetermined volume 68 and is then subjected to a fluctuating magnetic field as described for a duty cycle and period of time sufficient to properly influence the growth characteristics of the target tissue. In the most preferred embodiment, this influence will comprise the acceleration of growth characteristics to cause the proliferation and growth of tissue cells, whereas in another embodiment this influence will act to retard growth and proliferation. While the length of time necessary for successful treatment may vary, it is anticipated that up to about 100 days of treatment of a bone non-union to stimulate bone growth will provide beneficial results. Longer treatment may be desirable in certain applications.

In another embodiment of the present invention, values for q and m are determined with reference to a preselected ionic species. It will be known by those skilled in the art that the biochemical milieu of living tissue comprises a mixture of various ions in the intercellular and interstitial fluid. These ions include potassium ions, magnesium ions, sodiums ions, chloride ions, phosphate ions, sulfate ions, carbonate ions, bicarbonate ions and the like and various ions formed by the dissociation of amino acids, proteins, sugars, nucleotides and enzymes. Applicants have found that by utilizing the values of charge and mass for a preselected ion in the equation set forth above, which will be recognized by those skilled in the art as the cyclotron resonance relationship solved for $f_c/B$, ratios of frequency to magnetic flux density can be determined which serve to regulate growth characteristics of living tissue in accordance with the present invention. Evidence to date indicates that by using the charge-to-mass ratio of a preselected ion, a specific cyclotron resonance frequency for the ion can be determined. By then tuning tissue growth regulator 20 to maintain a combined magnetic flux density having the proper cyclotron resonance frequency, living tissue containing the preselected ion can be treated to bring about changes in growth characteristics. Again, evidence indicates that the beneficial results of the present invention in this embodiment are achieved when the preselected ion absorbs energy from the magnetic field of the present invention having the desired parameters. It is believed that this increase in energy promotes the transmembrane movement of the preselected ion across the cell membrane of one or more cell types comprising the target tissue. By enhancing the transmembrane movement of preselected ions in this manner, cell growth and tissue development can be increased or decreased by the present invention. For increasing the growth of bone tissue, it is preferred that the preselected ion comprise $Ca^{++}$ or $Mg^{++}$. To retard or inhibit bone growth, it is preferred that the preselected ion comprise $K^+$.

It will be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 68 which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. For example, if it necessary to maintain a frequency of 15 Hz and an average flux density of 1.95×10$^{-5}$ Tesla to affect growth characteristics of the target tissue, changes in the local field which would otherwise cause unwanted deviations in the combined magnetic flux density must be corrected by increasing or decreasing the applied magnetic flux density accordingly. This is most preferably performed by the microcontroller in connection with both the field generating means and the field-sensing device. Alternatively, as stated, if changes in the combined magnetic flux density along the axis will occur due to changes in the orientation of tissue growth stimulator 20 with respect to the local magnetic field, the frequency of the oscillations can then be changed so that the preferred therapeutic ratio is maintained. Once again, it is important to realize that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Referring now to FIG. 2 of the drawings, each field coil 42, 44 preferably has up to about 3000 turns or loops of conducting wire, the diameter d of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 50 may be produced by a sinusoidal signal or from a full-wave rectified signal applied to field coils 42, 44. It may also be appropriate in some instances to reduce components of the local magnetic field which are not parallel to predetermined axis 50 to zero through the use of additional coils positioned at right angles to treatment heads 30, 32 to create an opposite but equal field, but this is not deemed necessary. It may also be suitable to reduce the local magnetic field component to zero throughout treatment using additional coils or the like.

Figure 6:
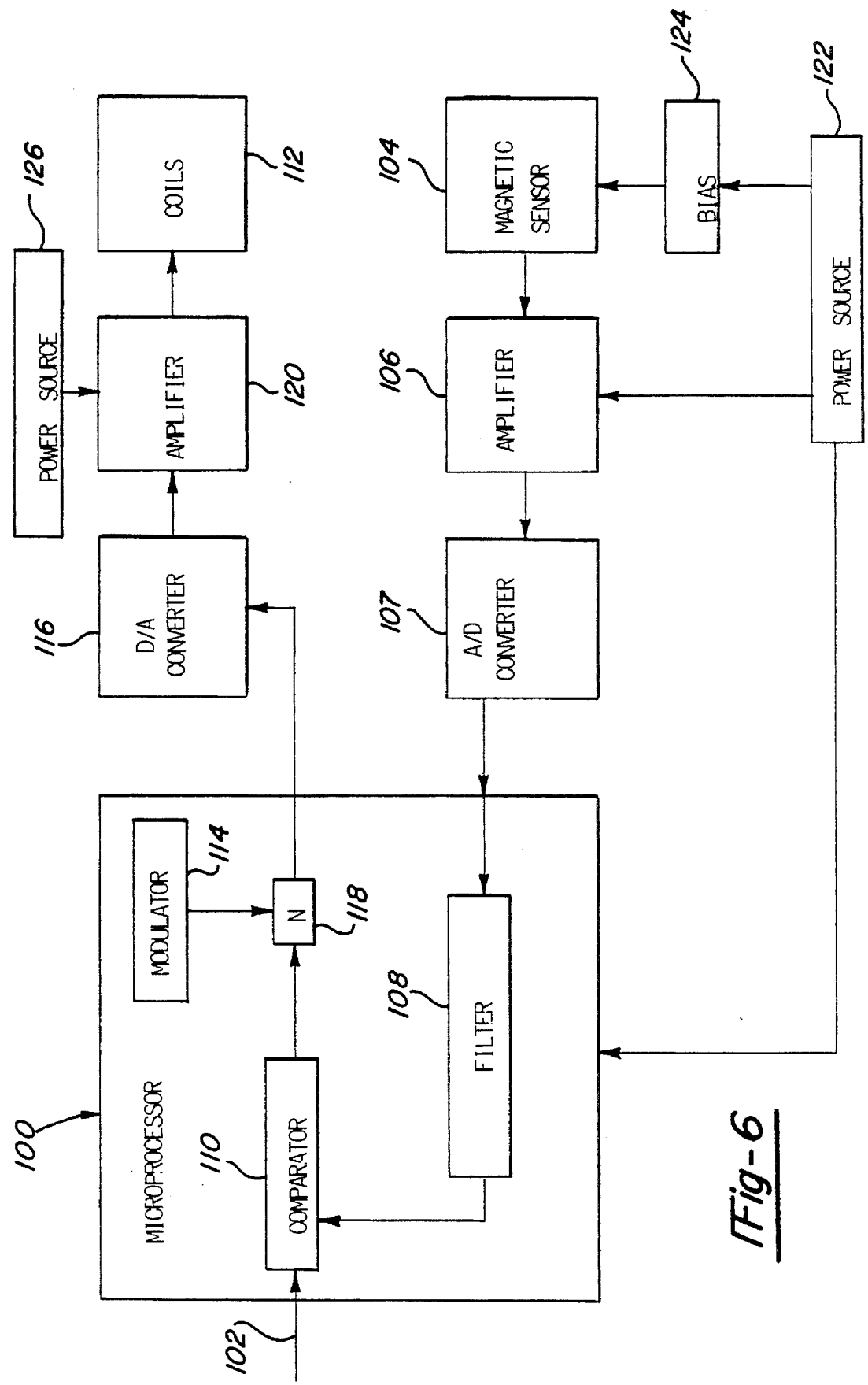
FIG. 6 is a block diagram of an embodiment of the present invention in which the circuit of the inventive apparatus is arbitrarily divided into convenient functional sections.

Referring now to FIG. 6 of the drawings, a block diagram is shown which depicts one preferred arrangement of the circuits of tissue growth regulator 20 in functional segments. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined axis through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect device which, as will be known by those skilled in the art, produces an analog signal. The magnetic field sensor 104 constantly monitors the composite magnetic field, sending a signal to microprocessor 100. It will be understood that the output of a Hall-effect magnetic sensor is relatively small; thus, magnetic field sensor amplifier 106 is provided by which the signal from magnetic field sensor 104 is amplified, for example, up to three thousand times its original value. Since a Hall-effect device produces an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 106 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. In this embodiment, software filter 108 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of magnetic growth regulator 20 with respect to the ambient field component. Hence, the time constant of filter 108 should be such that momentary fluctuations are filtered out.

Microprocessor 100 includes logic which calculates the non-zero net average value of the composite magnetic flux density. This non-zero average value is then compared at comparator 110 in microprocessor 100 to the predetermined dc reference or offset value which is input into microprocessor 100 via input 102. It should be noted that this reference value is preferably established by dedicated circuitry in microprocessor 100, although variable input means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion of the present invention, it will be understood that software field modulator 114 of microprocessor 100 in the preferred embodiment of the present invention is preset to a fixed, predetermined frequency to produce the desired predetermined, growth-regulating ratio of frequency-to-magnetic flux density value. In another embodiment, the feedback system of the present invention is such that changes in the composite magnetic flux density are measured, whereupon microprocessor 100 determines the necessary change in frequency to maintain the predetermined relationship. In that embodiment, software field modulator 114 produces the requisite ac frequency. It is again preferred that digital-to-analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 112 in the desired manner. Hence, the composite field is held substantially constant despite changes in the ambient component.

While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

Having fully described the apparatus of the present invention, including its manner of construction, operation and use, the method of the present invention will now be described. It is to be understood that this description of the method incorporates the foregoing discussion of the novel apparatus. In this aspect, the present invention provides a method of regulating the growth characteristics of living tissue. This is achieved in one embodiment by generating a fluctuating, directionally-oriented magnetic field which projects through the target tissue. A number of magnetic field generating means are suitable for this purpose, but the tissue growth stimulator previously described is preferred for use herein. The magnetic field so generated has a magnetic flux density of precisely controlled parameters which passes through the target tissue parallel to a predetermined axis projecting through the tissue. As will be known by those skilled in art and as has been clearly explained, the local magnetic field to which the target tissue is subjected will have a component which is parallel to the predetermined axis and which thus aids or opposes the applied or generated magnetic field along the axis. At times, the local component may be zero. In the method of the present invention, the density of this combined magnetic flux, and more specifically the average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of regulating growth characteristics of living tissue by creating a magnetic field which penetrates the tissue and which has a predetermined relationship between frequency of oscillation and average flux density. The predetermined relationship or ratio of frequency-to-field magnitude is determined with reference to the equation:

$$f_c/B = q/(2\pi m)$$

where $f_c$ is the frequency of the combined magnetic field along the predetermined axis in Hertz, B is non-zero net average value of the magnetic flux density of the combined magnetic field parallel to the axis in Tesla, q/m is in Coulombs per kilogram and has a value of from about $5\times10^5$ to about $100\times10^6$. B preferably has a value not in excess of about $5\times10^{-4}$ Tesla.

In order to create this fluctuating magnetic field having the desired parameters, the composite magnetic field parallel to the predetermined axis is constantly monitored. As stated, this is preferably carried out with a Hall effect device or the like which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, the method of the present invention includes the steps of creating and maintaining a predetermined relationship between the frequency of a fluctuating magnetic field to the flux density of the field. In particularly preferred embodiments, the ratio of frequency-to-flux density is determined with reference to the values: a frequency of 16 Hertz and an average flux density of $2.09\times10^{-5}$ Tesla. This combination of frequency and flux density is particularly useful in stimulating bone growth.

The following frequency and corresponding Flux density is useful in retarding bone growth: 16 Hertz and $4.09\times10^{-5}$ Tesla.

In a preferred embodiment of the method of the present invention, the ratio of frequency-to-flux density is determined by selecting a preselected ion present in the interstitial or intracellular fluids associated with the target tissue and tuning the fluctuating composite magnetic flux density to the specific cyclotron resonance frequency for the ion. The preferred ions for stimulating bone growth are $Ca^{++}$ and $Mg^{++}$. The preferred ion for inhibiting bone growth is $K^+$ Ions which may be useful in the present invention are set forth in the following table for purposes of illustration and limitation:

Hydrogen, $H^+$

Lithium, $Li^+$

Sodium, $Na^+$

Chlorine, $Cl^-$

Bicarbonate, $HCO_3^-$

Hence, in addition to the apparatus of the present invention, the present invention provides a method for controlling growth characteristics of living tissue which includes the steps of creating a fluctuating magnetic field of predetermined frequency and flux density along an axis projecting through a predetermined volume and positioning a target tissue within this predetermined space such that it is exposed to the fluctuating magnetic field. The predetermined parameters of the fluctuating magnetic field are determined by measuring the net average value of the combined magnetic flux density parallel to the predetermined axis through the tissue, where the combined magnetic field is the sum of the local magnetic field along the predetermined axis and the applied magnetic field. The frequency and/or magnitude of the applied magnetic flux density is then adjusted to produce a combined magnetic field along the axis having a predetermined ratio of frequency-to-flux density. This predetermined ratio influences the growth characteristics of the target tissue. The tissue is exposed to the fluctuating magnetic field for a duty cycle and a period of time sufficient to properly affect the growth characteristics of the tissue.

The following examples are provided to further describe and illustrate the present invention and are in no way intended to limit the scope of the appended claims.

EXAMPLE A

Twelve well plates were prepared by placing a sterile SS screen and a raft formed of a section of sterile triangular lens paper into each well. 0.5 ml of prepared BGJb medium to which antibiotics had been added was then introduced into each well which was sufficient to float each raft. Petri dishes were then prepared by placing squares of either sterile unbleached muslin or gauze sponges into each dish. The gauze sponges were moistened with a small amount of prepared Hank's Balanced Salt Solution (HBSS) medium. Eight-day old incubated chick eggs (white leghorn) were candled, from which 26 embryohated eggs were selected. Chick femurs were explanted to the gauze sponges and then moved to the muslin for cleaning. The identity of right and left femurs was maintained throughout the procedure. The length of each femur was then measured to the nearest 0.1 millimeter and the measurement recorded. Sets of control plates and sets of experimental plates were then designated. The left femurs were placed in the wells of the control plates and right femurs were placed in the wells of the experimental plates. Two femurs were placed in each well and each well was numbered. Throughout the procedure, the medium was replenished every other day. Throughout the test, both control and experimental femurs were exposed to the ambient magnetic field of the test facility. In addition, an applied, directionally-oriented fluctuating magnetic field was generated by a pair of Helmholtz coils to which the experimental femurs were exposed in the following manner. The composite magnetic flux density along a predetermined axis projecting through the femurs was measured with a magnetometer. One set of experimental plates were exposed to a composite magnetic flux, that is, the combined ambient field and applied field along the axis which fluctuated at a frequency of 16 Hz and a peak-to-peak amplitude of $3.0 \times 10^{-5}$ Tesla. For this set of experimental plates, the average magnetic flux density of the composite magnetic field parallel to the axis was maintained at $2.09 \times 10^{-5}$ Tesla. This corresponds to the frequency to magnitude ratio for $Ca^{++}$ using the cyclotron resonance relationship of the present invention. A second set of experimental plates were exposed to a combined or composite magnetic field in the same manner where the frequency was set at 16 Hz, but the average flux density along the axis was maintained at $4.09 \times 10^{-5}$ Tesla. This corresponds to the frequency to magnitude ratio for $K^+$ using the cyclotron resonance relationship. A third set of experimental plates were exposed to a fluctuating composite magnetic field in this fashion where the frequency of the fluctuations was 16 Hz and the average flux density was maintained at $1.27 \times 10^{-5}$ Tesla which corresponds to the frequency to magnitude ratio for $Mg^{++}$ using the cyclotron resonance relationship. The parameters of the fluctuating magnetic fields were maintained at these predetermined ratios for the duration of the treatment, seven days. Again, the control plates were exposed only to the ambient field. Following treatment, the chick femurs were fixed with 0.7 ml of 10% NBF. The length and mid-shaft diameter of each femur was measured and recorded. The ratio of length to mid-shaft diameter was determined for each femur.

In Table III, the mean lengths and standard deviation before ($T_0L$) and after ($T_7L$) treatment are set forth for the control and experimental femurs in the $Ca^{++}$ experiments.

The value of the mean and standard deviation for length/diameter is also set forth.

TABLE III

|  | Control | | | Experimental | | |
| --- | --- | --- | --- | --- | --- | --- |
|  | $T_0L$ | $T_7L$ | $T_7L/D$ | $T_0L$ | $T_7L$ | $T_7L/D$ |
| x | 4.7 | 8.15 | 9.53 | 4.7 | 9.4 | 7.8 |
| SD | 0.3 | 0.5 | 1.3 | 0.3 | 0.75 | 1.0 |

The results indicate that those chick femurs treated in accordance with the present invention were 15% longer, 41% thicker and 22% more robust (length/diameter) than the control femurs.

In Table IV, the mean lengths and standard deviation before and after treatment are set forth for the control and experimental femurs in the $K^+$ experiments. The value of the mean and standard deviation for length/diameter is also set forth.

TABLE IV

|  | Control | | | Experimental | | |
| --- | --- | --- | --- | --- | --- | --- |
|  | $T_0L$ | $T_7L$ | $T_7L/D$ | $T_0L$ | $T_7L$ | $T_7L/D$ |
| x | 4.7 | 8.1 | 9.9 | 4.7 | 7.6 | 10.3 |
| SD | 0.2 | 0.5 | 0.2 | 0.2 | 0.4 | 0.6 |

The results indicate that those chick femurs treated in accordance with the present invention were 7% shorter, 9% thinner and 4% more gracile (length/diameter) than the control femurs.

In Table V, the mean lengths and standard deviation before and after treatment are set forth for the control and experimental femurs in the $Mg^{++}$ experiments. The value of the mean and standard deviation for length/diameter is also set forth.

TABLE V

|  | Control | | | Experimental | | |
| --- | --- | --- | --- | --- | --- | --- |
|  | $T_0L$ | $T_7L$ | $T_7L/D$ | $T_0L$ | $T_7L$ | $T_7L/D$ |
| x | 4.7 | 7.6 | 9.9 | 4.7 | 8.4 | 8.0 |
| SD | 0.3 | 0.5 | 0.7 | 0.3 | 0.8 | 0.8 |

The results indicate that those chick femurs treated in accordance with the present invention were 10.5% longer, 37.3% thicker and 19.2% more robust (length/diameter) than the control femurs.

EXAMPLE B

Batches of twelve skeletally mature white rabbits were divided randomly into groups of three each. Each rabbit was anaesthetized, then the lateral surface of each leg (knee to ankle) was shaved and prepared for surgery. A 2.0 cm incision was made beginning at the knee and extending toward the ankle along the lateral surface of the leg. The fibula was exposed by division along the anterior/lateral compartment line. An incision was made in the periosteum of each fibula, and the periosteum was reflected dorsally and ventrally for a proximodistal distance of 1.5 cm, beginning 5 mm from the union of tibia and fibula. The periosteum of the right fibula was allowed to return to place, and the wound was closed in layers. The right fibula thus served as a sham-operated control. The left fibula was treated similarly, except that a 1 cm section of bone was excised, and the periosteum was preserved across the gap. The wounds were likewise closed in layers. The left legs thus served as operated test specimens. After surgery, the animals were given analgesics and returned to cages for recovery.

The first group of three animals were returned to their cages and given no further treatment. The first group served as controls. The second group were placed in cages of identical proportions, placed between pairs of Helmholtz coils. The composite magnetic flux density along a predetermined axis corresponding to the axis of the pair of coils and projecting through the bodies of the animals, including the fibulae, was measured with a magnetometer. The coils were used to apply a directionally-oriented fluctuating magnetic field to the entire body of each animal. Thus, each animal in this group was exposed to a composite magnetic flux, that is, the combined ambient field plus an applied field along the axis of the coils, which fluctuated at 35.6 Hz, with a peak-to-peak amplitude of $3.0 \times 10^{-5}$ Tesla of the AC component with the static magnetic flux density parallel to the cage axis at $4.65 \times 10^{-5}$ Tesla, and these conditions corresponded to the frequency-to-magnitude ratio for $Ca^{++}$ ions, using the cylotron resonance relationship of the present invention. The above described magnetic flux was applied for 24 hours per day for four weeks.

The third group of three animals were treated with an identical combined static and alternating magnetic flux, except that the duty cycle was reduced to 3 hours per day.

The fourth group of animals were treated with a similar set of magnetic fluxes for 24 hours per day, except that the frequency was adjusted to 60.5 Hz, which, given the static magnetic flux density parallel to the cage axis of $4.75 \times 10^{-5}$ Tesla, corresponded to the frequency to magnitude ratio for $Mg^{++}$ ions, using the cyclotron resonance relationship of the present invention. The parameters for all fields were maintained for the duration of the experiment, four weeks.

At the end of the experiment, the animals were sacrificed, and the legs were removed by disarticulation at the knee and ankle. The legs were x-rayed in the frontal plane (A-P axis). From these x-rays, the width of the callus filling the osteotomy defect was measured at its narrowest point in the gap. The diameter of the fabella, a small sesamoid bone near the knee was also measured from the x-rays. Subsequently, the muscular tissue was stripped from the tibia and fibula, and the bones were clamped in a fixation device. A stylus attached to a force transducer was then applied to the fibula, and it was anteriorly or posteriorly bent to the extent of 1 mm from its normal proximodistal axis, at the distance of 2 cm from the attachment of the fibula to the tibia, i.e., 1.5 cm proximal to the distal end of the osteotomy gap. The stiffness (force/mm displacement) of the operated side was then compared to that of the sham-operated side of the leg, and to the operated side of the control legs.

In Table VI, The mean callus widths and standard deviations for all groups are set forth, plus a statistical comparison of experiments and controls. In Tables VI through VIII, t is student's t value.

TABLE VI

| Group | Callus Widths | |
|---|---|---|
| | Width | Variation |
| $Ca^{++}$ 24 Hours | 4.16 mm | S.D. 0.61 |
| $Ca^{++}$ 3 Hours | 3.72 mm | S.D. 0.55 |
| $Mg^{++}$ 24 Hours | 4.24 mm | S.D. 0.79 |
| Control | 2.57 mm | S.D. 0.36 |

Ca/24 vs. Control - t = 3.55, p < .05
Ca/03 vs. Control - t = 5.05, p < .05
Mg/24 vs. Control - t = 3.07, p > .05

In Table VII, the diameters of the fabellae are compared by groups, and are set forth in the same manner as for Table VI.

TABLE VII

| Group | Diameter | Variation |
|---|---|---|
| $Ca^{++}$ 24 Hours | 3.18 mm | S.D. 0.12 |
| $Ca^{++}$ 3 Hours | 3.17 mm | S.D. 0.34 |
| $Mg^{++}$ 24 Hours | 3.76 mm | S.D. 0.25 |
| Control | 2.22 mm | D.S. 0.38 |

Ca/24 vs. Control, t = 3.41, p < .05
Ca/03 vs. Control, t = 2.63, p < .06
Mg/24 vs. Control, t = 5.35, p < .05

In Table VIII, the relative stiffnesses of the experimental and control operated sides to their opposite sham-operated sides are compared and set forth. Comparisons between control and experimental values are also set forth.

TABLE VIII

| Group | Relative Stiffness | |
|---|---|---|
| | Ratio | Variation |
| $Ca^{++}$ 24 Hours | .631 | S.D. 0.383 |
| $Ca^{++}$ 3 Hours | .233 | S.D. 0.004 |
| $Mg^{++}$ 24 Hours | .594 | S.D. 0.571 |
| Control | .194 | D.S. 0.170 |

Ca/24 vs. Control = +320%
Ca/03 vs. Control = +120%
Mg/24 vs. Control = +255%

From these data, it is evident that an application of the method of the present invention materially stimulates the growth and regeneration of bone in whole animals, as compared to animals not stimulated according to the method of the present invention. The amount of callus in the region of a defect is increased, the stiffness of the repair, and hence its weight-bearing ability, is increased. The growth of the bones is enhanced generally, as evidenced by the diameters of the fabellae, bones not subjected to any surgical treatment.

While particular embodiments of this invention are shown and described herein, it will be understood, of course, that the invention is not to be limited thereto, since many modifications may be made, particularly by those skilled in the art. in light of this disclosure. It is contemplated, therefore, by the appended claims, to cover any such modifications as fall within the true spirit and scope of this invention.

What is claimed is:

1. A method for regulating the growth characteristics of tissue in vivo in a human subject, comprising the steps of:

positioning a magnetic field generating means adjacent to a living human subject in an ambient magnetic field having an ambient static component;

generating an applied magnetic flux with said magnetic field generating means, said applied magnetic flux extending through a region of tissue of said human subject along an axis projecting through said region of tissue, said applied magnetic field having both a time varying component and an applied static component; and maintaining a ratio between the rate at which said time varying component changes and the magnitude of said applied static component of said applied field, wherein said ratio regulates the development of said tissue.

\* \* \* \* \*

UNITED STATES PATENT AND TRADEMARK OFFICE
CERTIFICATE OF CORRECTION

PATENT NO. : 5,458,558
DATED : October 17, 1995
INVENTOR(S) : A.R. Liboff, B.R. McLeod and S.D. Smith It is certified that error appears in the above-indentified patent and that said Letters Patent is hereby corrected as shown below:

Column 1, Line 43, delete "Interaction" and insert --interaction--.

Column 2, Line 38, delete "Fractured" and insert --fractured--.

Column 14, Line 9, after "K$^+$" insert --.--.

Column 14, Line 55, delete "embryohated" and insert --embryonated--.

Signed and Sealed this

Twentieth Day of February, 1996

Attest:

BRUCE LEHMAN

*Attesting Officer*  *Commissioner of Patents and Trademarks*